United States Patent [19]
Takata et al.

[11] Patent Number: 5,431,055
[45] Date of Patent: Jul. 11, 1995

[54] SURFACE MEASURING APPARATUS USING A PROBE MICROSCOPE

[75] Inventors: Keiji Takata, Tokorozawa; Hiromichi Shimizu, Hoya; Shigeyuki Hosoki, Hachioji; Sumio Hosaka, Tokyo, all of Japan

[73] Assignee: Hitachi, Ltd., Tokyo, Japan

[21] Appl. No.: 58,231

[22] Filed: May 10, 1993

Related U.S. Application Data

[63] Continuation of Ser. No. 833,613, Feb. 13, 1992, Pat. No. 5,222,396, which is a continuation of Ser. No. 480,675, Feb. 15, 1990, abandoned.

[30] Foreign Application Priority Data

Feb. 17, 1989 [JP] Japan .................. 1-036124

[51] Int. Cl.$^6$ ........................... G01N 29/24
[52] U.S. Cl. ........................... 73/618; 73/634; 73/643; 250/307; 250/423 F
[58] Field of Search .............. 73/643, 618, 633, 105, 73/634, 601; 250/306, 307, 423 F

[56] References Cited

U.S. PATENT DOCUMENTS

| | | | |
|---|---|---|---|
| 3,577,774 | 5/1971 | Steffens et al. | 73/643 |
| 4,618,767 | 10/1986 | Smith et al. | 250/311 |
| 4,668,865 | 5/1987 | Gimzewski et al. | 250/306 |
| 4,902,892 | 2/1990 | Okayama et al. | 250/307 |
| 4,987,303 | 1/1991 | Takase et al. | 73/105 |
| 5,003,815 | 4/1991 | Martin et al. | 73/105 |
| 5,107,112 | 4/1992 | Yanagisawa et al. | 250/306 |

OTHER PUBLICATIONS

"Acoustic Detector and Generator" (IBM Technical Bulletin) (Apr. 1987) (vol. 29 No. 11).
"Effect of electronic strain on photoacoustic generation in Silicon", by R. G. Stearns and G. S. Kino, Appl. Phys. Lett. 47(10), Nov. 15, 1985, pp. 1048–1050.
"Visualization of surface elastic waves on structural materials" by G. Alers, M. A. Temison, R. B. Thompson, and B. R. Tittman (Jul. 1973) Ultrasonics.
"Photostriction Effect in Germanium" by T. Figielski, Phys. Status Solidi, vol. 1, 306 (1961) pp. 306–316.
"Generation of Elastic Waves by Transient Surface Heating" by R. M. White (Journal of Applied Physics, vol. 34, No. 12, Dec. 1963).
"Elastic Wave Generation by Electron Bombardment or Electromagnetic Wave Absorption" by R. M. White (Communications, Oct. 29, 1962).

Primary Examiner—Hezron E. Williams
Assistant Examiner—Rose M. Finley
Attorney, Agent, or Firm—Antonelli, Terry, Stout & Kraus

[57] ABSTRACT

A scanning tunneling microscope, in which the gap between a tip having a keenly sharpened end and a sample is narrowed to let flow a tunneling current between them and thereby allow observation of the surface of the sample, a strain wave detecting device is disposed on the sample or in the vicinity of the sample to detect strain waves generated within the sample. By modulating the value of the above described tunneling current, strain waves are generated within the sample. The strain waves are detected by the above described strain wave detecting device. On the basis of the amplitude information and phase information of detected strain waves, physical information regarding the inside of the sample is obtained.

20 Claims, 13 Drawing Sheets

SURFACE MEASURING APPARATUS USING A PROBE MICROSCOPE

This is a continuation of application Ser. No. 07/833,613, filed Feb. 13, 1992, now U.S. Pat. No. 5,22,396, which is a continuation of Ser. No. 07/480,675, filed Feb. 15, 1990, now abandoned.

BACKGROUND OF THE INVENTION

The present invention relates to improvement of a scanning tunneling microscope and in particular to a tunneling acoustic microscope so improved as to be suitable for observing lattice strain caused within a sample.

Conventional scanning tunneling microscopes (hereafter abbreviated to STMs) are discussed in U.S. Pat. No. 4,618,767, U.S. Pat. No. 4,668,865, and Appl. Phys. Lett. 40(2), 1982, pp. 178–180.

The configuration based upon the principle of an STM will now be described. That is to say, a tungsten tip is so disposed as to be close to the surface of a conductive sample, and a tunneling current is let flow between them. The tip or the sample is scanned while the gap between the tip and the sample is so adjusted that the tunneling current may be kept constant. Topographies on the surface of the sample are thus obtained.

In the above described prior art, derivation of topographies such as corrugation on the surface of the sample is mainly described. Derivation of information concerning the inside of the sample and concrete means for that purpose are not presented. Further, the case where the sample is an insulator is not considered.

SUMMARY OF THE INVENTION

An object of the present invention is to obtain information concerning the inside of a sample such as strain or crack in a crystal sample, which cannot be observed by a conventional STM.

Another object of the present invention is to make measurement of the gap (vacuum gap) between the tip and the sample and observation of topographies on the insulator surface during the STM measurement possible.

The above described objects are achieved by detecting strain waves, which are caused within the sample by periodically increasing or decreasing (modulating) the tunneling current incident upon the sample, by using a transducer comprising a piezoelectric plate.

Measurement of the vacuum gap and observation of the insulator surface are achieved by bringing the tip into contact with the sample surface to cause strain in the sample and detecting that strain.

Since the amplitude and phase of strain waves generated within the sample by modulating the tunneling current reflects the physical information concerning the inside of the sample, images representing its distribution are obtained.

If the tip extremely approaches the sample surface, atomic force exerted between them causes strain in the sample. since it is possible to know the distance between the tip and the sample surface by sensing this strain, measurement of vacuum gap and observation of the surface structure of the insulator during the STM measurement becomes possible. By transmitting the atomic force exerted between the tip and the sample to a distant location as strain waves and detecting it by means of a transducer or a specially provided STM, it is possible to distinguish between attractive force and repulsive force and know even the magnitude of them. In the same way, it is also possible to know the magnetic force and electric force exerted between the tip and the sample.

DESCRIPTION OF PREFERRED EMBODIMENTS

Figure 1:
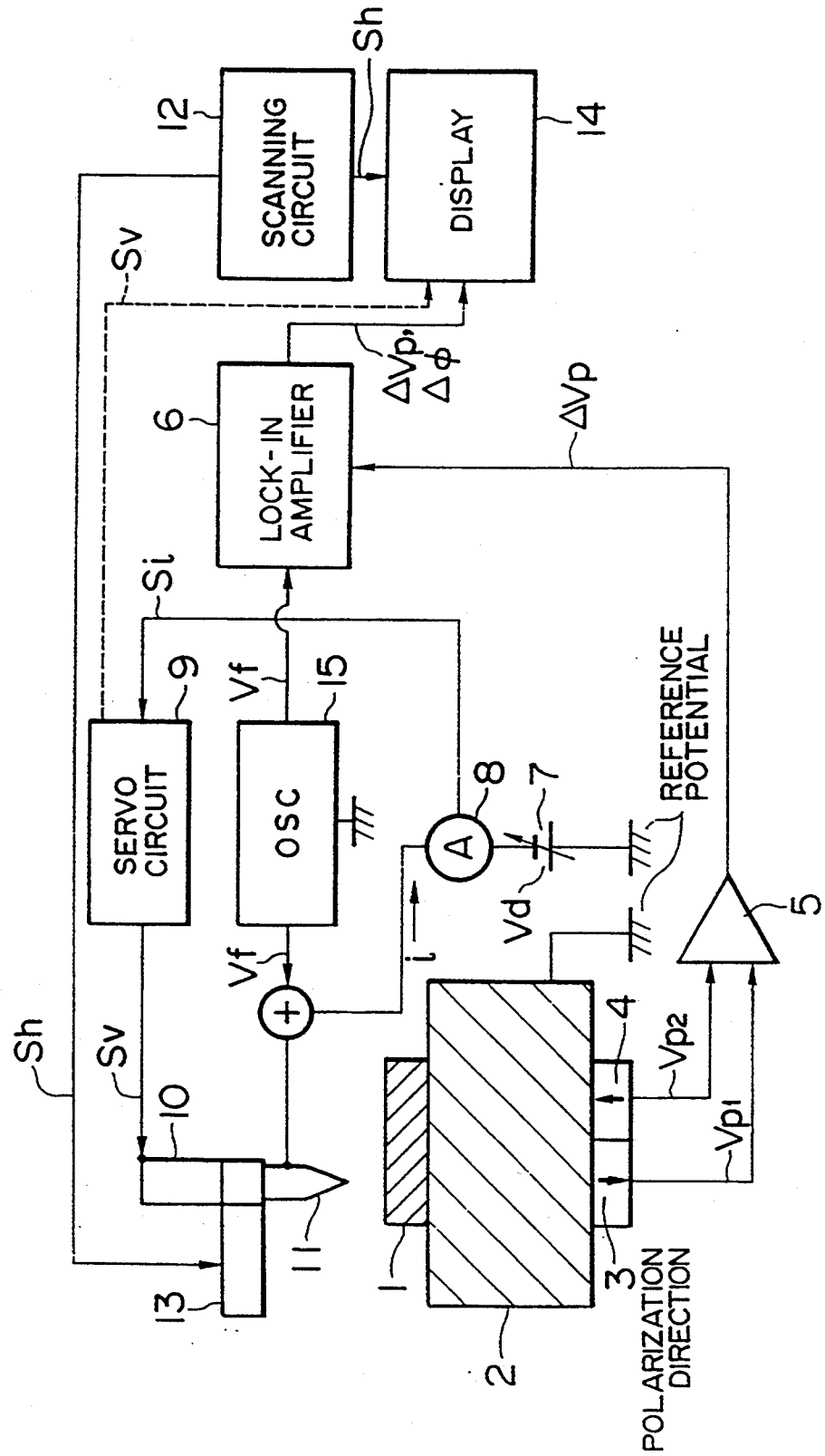
FIG. 1 is a block diagram showing an embodiment of the present invention.

An embodiment of the present invention will hereafter be described by referring to FIG. 1. A conductive sample 1 is coupled to the surface of a conductive block 2, whereas piezoelectric plates 3 and 4 are coupled to the rear surface of the block 2. The piezoelectric plates 3 and 4 have the same volume and material excepting that they are opposite in polarization direction. Voltages $V_{P1}$ and $V_{P2}$ respectively induced in the two piezoelectric plates undergo subtraction in a differential amplifier 5, and a differential output $\Delta V_P$ is inputted to a lock-in amplifier 6.

A metal tip 11 having a sharpened end is supplied with a DC voltage $V_d$ from power supply 7. If the tip 11 is made to approach the surface of the sample 1, a tunneling current i flows between them. This tunneling current i is detected by an ammeter 8. A resultant signal $S_i$ thus detected is inputted to a servo circuit 9. The servo circuit 9 outputs a drive signal $S_V$ to actuate a Z-positioner 10 which positions the tip 11 in the Z-direction with respect to the sample. The gap between the tip 11 and the sample 1 is thus adjusted so that the DC component of the tunneling current i may be kept constant. A scanning circuit 12 outputs a scanning signal Sh to scan the tip 11 in a two-dimensional way in a plane parallel to the sample face via the scanner 13. By displaying the drive signal $S_v$ supplied to the Z-positioner 10 on a display 14 in relation to the scanning signal $S_h$ supplied to the scanner 13, STM images are obtained.

AC voltage $V_f$ fed from an oscillator 15 is also supplied to the tip 11 so that it may be added to the above described DC voltage $V_d$. At the same time, this AC voltage $V_f$ becomes the reference signal of the lock-in amplifier 6. The frequency of the AC voltage $V_f$ fed from the oscillator 15 is equivalent to the resonant frequency of the piezoelectric plates 3 and 4 and is higher than the time constant of the servo circuit 9. As a result, the servo circuit 9 does not respond to the AC component of the tunneling current i changing in response to the AC voltage $V_f$ fed from the oscillator 15. Therefore, the tunneling current i is modulated by the frequency of the AC voltage $V_f$.

Since the magnitude of strain caused in the sample changes depending upon the amount of tunneling current incident upon the sample 1, strain generated on the surface of the sample is transmitted in the sample and in a block 2 as strain waves, the piezo-electric plates 3 and 4 being strained. Since the two piezoelectric plates are opposite each other in polarization direction, they are opposite each other in output voltage polarity. By applying subtraction processing to induced voltages $V_{p1}$ and $V_{p2}$ respectively of the piezoelectric plates 3 and 4 in the differential amplifier 5, therefore, the greater part of induction noise is cut. The lock-in amplifier 6 is able to output the amplitude $\Delta V_p$ of the output signal of the differential amplifier 5 and a phase shift $\Delta \phi$ of the phase of that output signal with respect to the phase of the AC voltage $V_f$. The amplitude $\Delta V_p$ and the phase shift $\Delta \phi$ can be displayed on a display 14 in relation to the scanning signal $S_h$. This is a scanning tunneling acoustic microscope image referred to in the present application.

Cause of occurrence of strain will now be described briefly. Electric strain occurring in a semiconductor crystal was already discussed by T. Figielski in 1961 (Phys. Status Solidi, Vol. 1,306 (1961)). Further, the magnitude of electric strain was compared with the magnitude of thermal strain by R. G. Stearns etc. in recent years (Appl. Phys. Lett., Vol. 47, 1048 (1985)). Electron-hole pairs generated by light change the crystal lattice constant. The magnitude of strain is proportionate to dEg/dP (where Eg is the energy gap and P is pressure) and density of electron-hole pairs.

In the STM, only electrons or holes instead of electron-hole pairs are injected with high density into a semiconductor sample. Strain caused by such a phenomenon was not yet discussed in detail. In case electrons are injected with high density into the conduction band, for example, the ratio of a change of energy level at the lowest end of the conduction band with respect to a change of lattice constant is important. In case many holes are injected into the valence band, proportions of changes of the energy level at the upper end and lower end of the valence band largely contribute to strain.

That is to say, it is possible to know the electron level (band) structure by examining the amplitude and phase of strain waves (such as whether expansion or contraction is caused in case holes are injected). Eventually, it is possible to know a shift in lattice constant caused by stress within the crystal.

This embodiment is optimum for measuring the distribution of internal stress caused by mismatch of lattice constant in a semiconductor device, which is fabricated by stacking a large number of layers comprising materials having different lattice constants by means of a technique such as molecular beam epitaxy, and for measuring the distribution of stress caused in the crystal by implantation of impurities.

If the voltage of the power supply 7 is set at mV order and the semiconductor sample is observed, thermal strain caused by the Peltier effect is observed. If electrons are injected from the metal tip into the sample, cooling (contraction) occurs in an n-type semiconductor whereas heating (expansion) occurs in a p-type semiconductor. That is to say, the polarity of the phase shift output $\Delta \phi$ fed from the lock-in amplifier 6 in case of p-type semiconductor is opposite to that in case of n-type semiconductor. Therefore, it is possible to definitely distinguish between them. Further, there is a p-n junction within the sample. If a current flows through the p-n junction, the Peltier effect occurs. As a result, information concerning the junction within the sample is obtained.

If the voltage of the power supply 7 is set at a higher value, heating by resistance within the sample is incurred. Irrespective of the direction of the tunneling current and electrical properties of the sample, heating (expansion) always occurs. The mechanism of strain occurrence in this case is nearly the same as that in case of an electron acoustic microscope. Contrasts of the resultant images are similar in those cases. However, a tunneling acoustic microscope, in which a large current can be injected into a narrow region at low voltage, is superior in resolution. An electron acoustic microscope is described in Japanese Journal of Applied Physics, Volume 51, No. 2 (1982), pp. 205–209.

Figure 2:
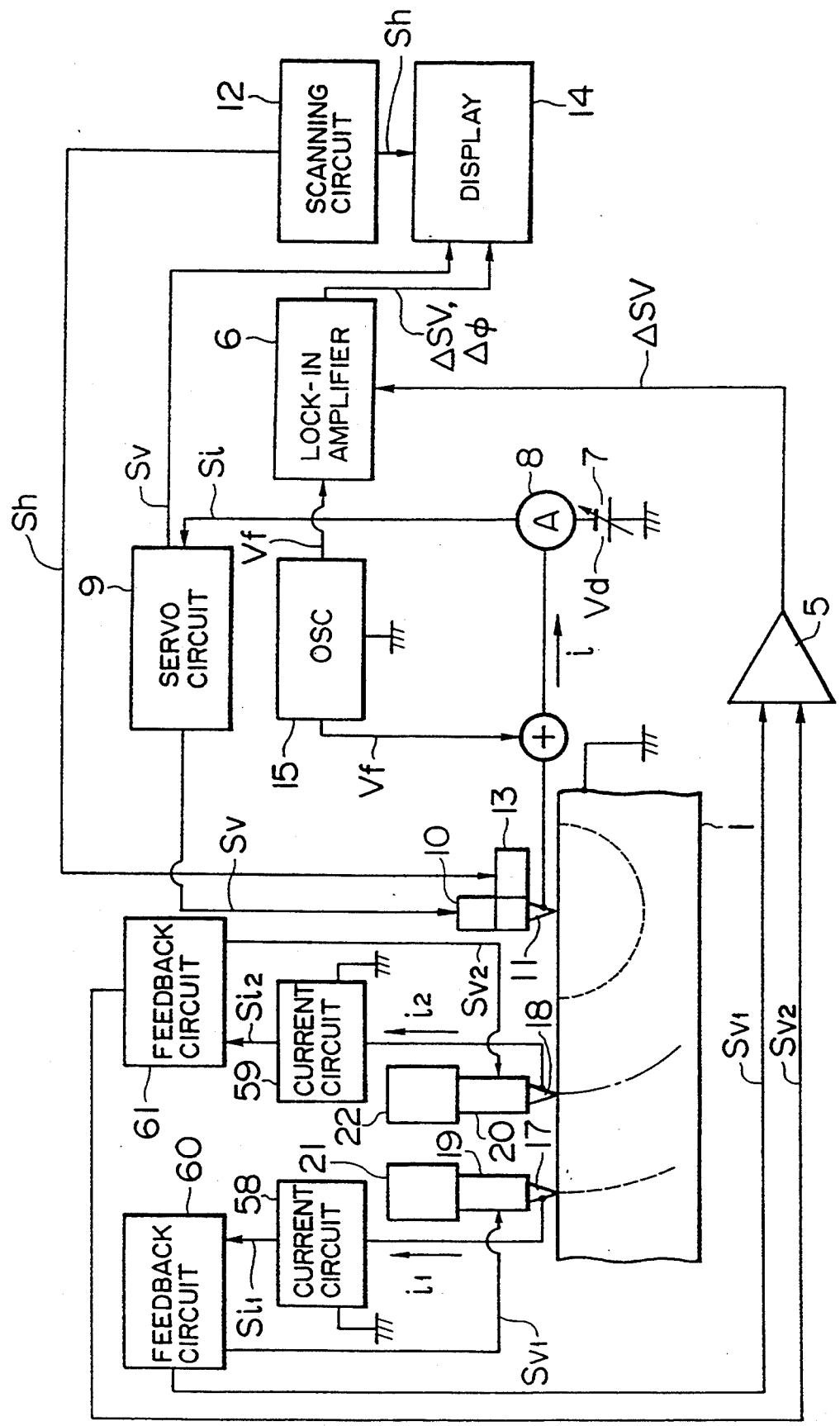
FIGS. 2 and 3 are diagrams showing the principle of a method for detecting strain waves.

A method for detecting strain waves using an STM and an atomic force microscope (hereafter abbreviated to AFM) will now be described. Since the STM and AFM can detect corrugation on an atomic level caused on the sample surface, they can be used for detection of strain waves having a very minute amplitude as well. An example of the configuration is shown in FIG. 2. Broken lines within the sample 1 represent the maximum amplitude of strain waves, and an unevenly broken line represents the position of amplitude 0. Suitable voltages are applied between a tip 17 and the sample 1 and between a tip 18 and the sample 1 respectively by current circuits 58 and 59. Currents (tunneling currents) $i_1$ and $i_2$ flowing between respective tips and the sample are measured. Feedback circuits 60 and 61 respectively expand or contract Z-positioners 19 and 20 so that values of these currents may become constant, respectively. As a result, the gap between the tip 17 and the sample 1 and the gap between the tip 18 and the sample 1 are kept constant. Owing to the functioning of moving mechanisms 21 and 22, tips 11, 17 and 18 are arranged nearly on a straight line, and the space between the tips 17 and 18 is so set as to be equal to half wavelength of the surface wave. Acoustic absorbing materials are applied to the end of the sample 1 to prevent reflection of the surface wave. When this method is used, amounts corresponding to amplitudes of the surface wave are detected as displacements of the tips 17 and 18, i.e., as output signals $S_{v1}$ and $S_{v2}$ respectively of the feedback circuits 60 and 61. By comparing amplitudes sensed by the tips 17 and 18, the attenuation constant of the surface wave is found. As a result, the amplitude at the origination source of strain (i.e., at the sample surface near the tip 11) can be estimated, and the absolute value of strain with respect to the amount of injected tunneling current i is found. Therefore, the elastic electric characteristic of the sample 1 is made clear.

The tips 17 and 18 may be positioned by the moving mechanisms 21 and 22 so that the phase difference between displacements of the tips 17 and 18 may become 180°. By doing so, the space between the tips 17 and 18 becomes equivalent to half wavelength of the surface wave, and the velocity of the surface wave is also found. Thereafter, imaging performed by scanning the tip 11 is executed.

Instead of the output voltages of the piezoelectric plates 3 and 4, as shown in FIG. 1, displacement signals of the tips 17 and 18 (i.e., output signals $S_{v1}$ and $S_{v2}$ respectively of the feedback circuits 60 and 61) are inputted to the differential amplifier 5. The function and configuration of FIG. 2 is the same as those of FIG. 1 with the exception of means for detecting strain waves. Under the state that the output frequency of the oscillator 15 is so high that the tips 17 and 18 may not follow it, output signals of the current circuits 58 and 59 (i.e., tunneling current values $i_1$ and $i_2$) are inputted to the differential amplifier 5.

Figure 3:
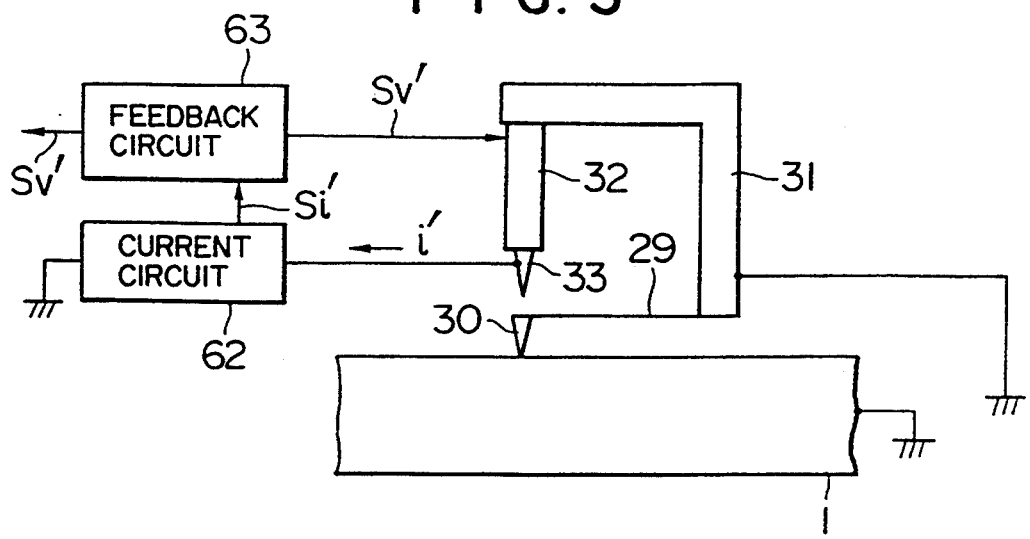

When waves on the surface of the sample 1 are to be detected without letting flow a current through the sample, an AFM is used as shown in FIG. 3. A tip 30 made of an insulating material is attached to one end of a cantilever 29 comprising a thin metal plate. The other end of the cantilever 29 is fixed to a conductive frame 31. A Z-positioner 32 and a conductive tip 33 are attached to the frame 31. Voltage is applied between the tip 33 and the cantilever 29 by a current circuit 62 to measure a current i' flowing between them. The feedback circuit 63 expands or contracts the Z-positioner 32 so that the current i' may have a constant value. The gap between the cantilever 29 and the tip 33 is kept constant. Since the tip 30 is an insulator, a current does not flow into the sample 1. Weak atomic force (repulsive force) is exerted between the tip 30 and the sample 1.

The surface wave of the sample is detected as displacement of the tip 33 via displacement of the tip 30. An output signal $S_v'$ of the feedback circuit 63 (i.e., a displacement signal of the tip 33) corresponds to the output signal of the piezoelectric plate 3 or 4 shown in FIG. 1, or the output signal of the feedback circuit 60 or 61 shown in FIG. 2.

In comparing detection of strain waves by piezoelectric plates with detection thereof by the STM and AFM, detection of up to a high frequency is possible in the former case, whereas a wave having a very minute amplitude can be measured, and the value of strain at the source of strain can be easily estimated in the latter case.

An example of measurement using a tunneling acoustic microscope will now be described by referring to the configuration of FIG. 1.

Figure 4:
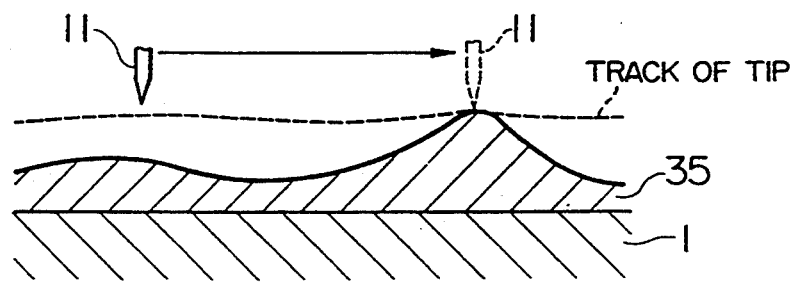
FIG. 4 is a schematic diagram showing the scanning state of the tip in an STM.

FIG. 4 shows how an insulative film 35 on the surface of the conductive sample 1 is observed by using an STM. Constant voltage is applied between the tip 11 and the sample 1. The tip 11 depicts a track as indicated by broken lines in FIG. 4 so that the tunneling current may become constant. Because of difference in dielectric constant between the film 35 and vacuum, the track of the tip 11 slightly reflects the shape of the film 35. At a position where the film 35 is thick, however, the tip 11 collides with a convex portion of the film 35. At this time, large strain waves are generated, and strong pulsive signals are outputted from the piezoelectric plates 3 and 4 shown in FIG. 1. By storing the position of occurrence of the pulse, the place where the film 35 is thick can be located on the STM image.

If contact of the tip 11 with the sample 1 occurs, the place where the tunneling current flows is changed by deformation of the tip end. The STM image thus becomes discontinuous and reproducibility is also hampered. If contact occurs, therefore, the voltage $v_d$ of the power supply 7 is raised and the gap between the tip 11 and the sample 1 is widened by the function of the servo circuit 9. As a result, a vacuum gap always exists between the tip 11 and the sample 1, resulting in an STM image with fine reproducibility. The object as described above can be also performed by decrease of the preset value of the tunneling current i instead of raising the voltage $V_d$ of the power supply 7.

In case there is a steep step on the surface of the sample, collision occurs unless the response speed of the servo circuit 9 is sufficiently high. At this time, collision can be avoided by making the scanning speed slow.

Figure 5:
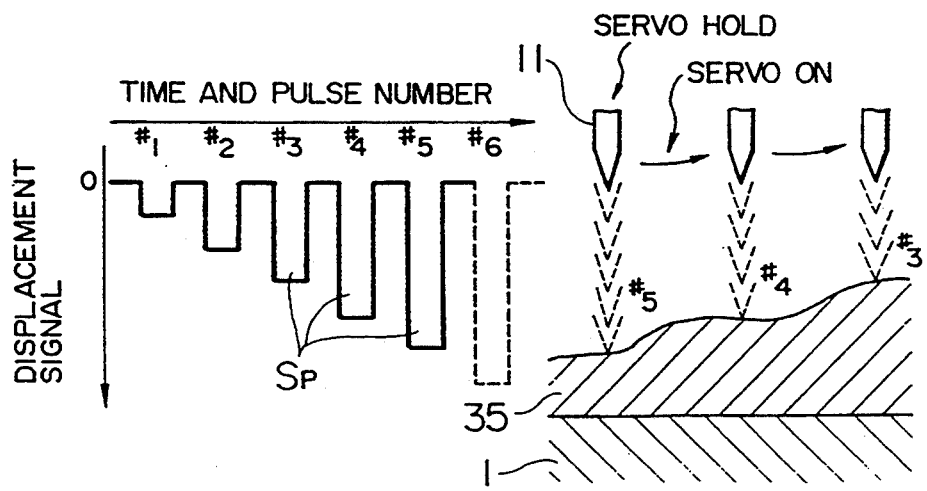
FIG. 5 is a schematic diagram showing how vacuum gap measurement is performed.
Figure 6:
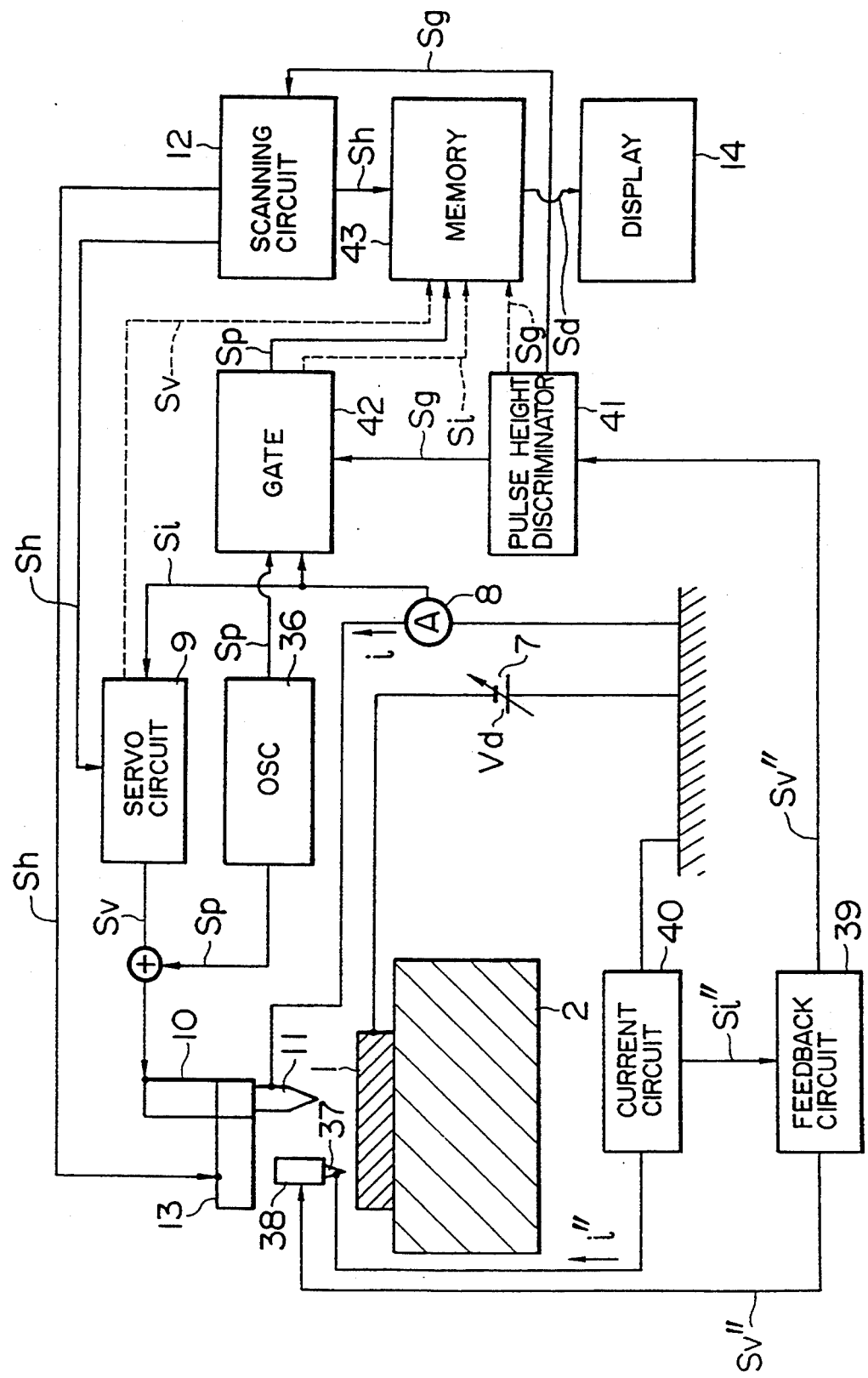
FIGS. 6 and 7 are block diagrams respectively showing other embodiments of the present invention.

An example of application of detection of strain caused by force exerted between the tip and the sample to collision prevention has hereto been described. However, application of the strain detection to measurement of a vacuum gap and observation of an insulator is also possible. This will now be described by referring to FIGS. 5 and 6. It is now assumed that the surface of the sample 1 whereon the insulative film 35 exists as shown in FIG. 4 is observed. The scanning circuit 12 shown in FIG. 6 raster-scans the tip 11 along the sample face 1. By the scanning signal $S_h$ fed from the scanning circuit 12, the output signal $S_V$ of the servo circuit 9 is held at each point and the tip 11 is stopped. Subsequently, a pulse signal $S_p$ fed from a pulse oscillator 36 is added to the output signal $S_v$ of the servo circuit 9 to make the tip 11 approach the sample 1 on the basis of the pulse height. As shown in FIG. 5, the pulse height of the pulse $S_p$ increases with time. At a certain pulse number, the tip 11 comes in contact with the sample surface. Strain caused at this time is detected by a strain detection system of STM scheme comprising a tip 37, a Z-positioner 38, a feedback circuit 39 and a current circuit 40. The value of strain is outputted to a pulse height discriminator 41 as an output signal $S_v''$ of the feedback circuit 39. During the STM measurement, force is exerted between the tip 11 and the sample 12. Even at a small pulse height, a strain signal is generated. When a large signal caused by contact between the tip 11 and the sample 1 is inputted, the pulse height discriminator 41 outputs a pulse signal $S_g$ to a gate 42. At this time, the gate 42 is opened, and the pulse height of the output pulse $S_p$ of the oscillator 36 at that time is inputted to a memory 43. If the tip 11 comes in contact with the sample 1 at a fifth pulse, for example, the gate 42 opens during the time between the fifth pulse and the sixth pulse. However, a pulse outputted from the oscillator 36 to the gate 42 is delayed by time of pulse spacing. The fifth pulse is thus inputted to the memory 43. At the same time as the gate 42 is opened, the oscillator 36 stops its output and the sixth pulse is not outputted. The output pulse $S_g$ of the pulse height discriminator 41 is inputted to the scanning circuit 12 as well, and the servo circuit 9 is released from its hold state. The tip 11 is scanned by a distance of one pitch. In FIG. 5, scanning is performed by such a method, and the fifth, fourth and third pulses are stored into the memory 43 at respective positions. It is understood that the pulse height (or pulse number) of pulses thus stored corresponds to vacuum gap.

By using this method of measurement, the vacuum gap can be measured. The thickness of the insulative film or the electrical characteristic of the sample becomes clear.

When the servo circuit 9 is in the hold state, the tunneling current i increases as the tip 11 is made to approach the sample 1. Strain caused thereby becomes a primary factor of error in vacuum gap measurement. At the time of servo hold, therefore, the voltage of the power supply 7 is simultaneously set at 0 volt to prevent the tunneling current from flowing.

By comparing the value of vacuum gap in case the tunneling current is let flow with that in case the tunneling current is not let flow, however, the amount of strain caused in the sample by the tunneling current can be measured. Further, the value of the tunneling current at the time of contact under the condition that the voltage value $v_d$ of the power supply 7 is kept constant reflects the thickness of the insulative film or conductivity of the sample face and hence it is useful information in surface observation. Therefore, it is also possible to store a tunneling current signal $S_i$ into the memory 43 via the gate 42.

Figure 7:
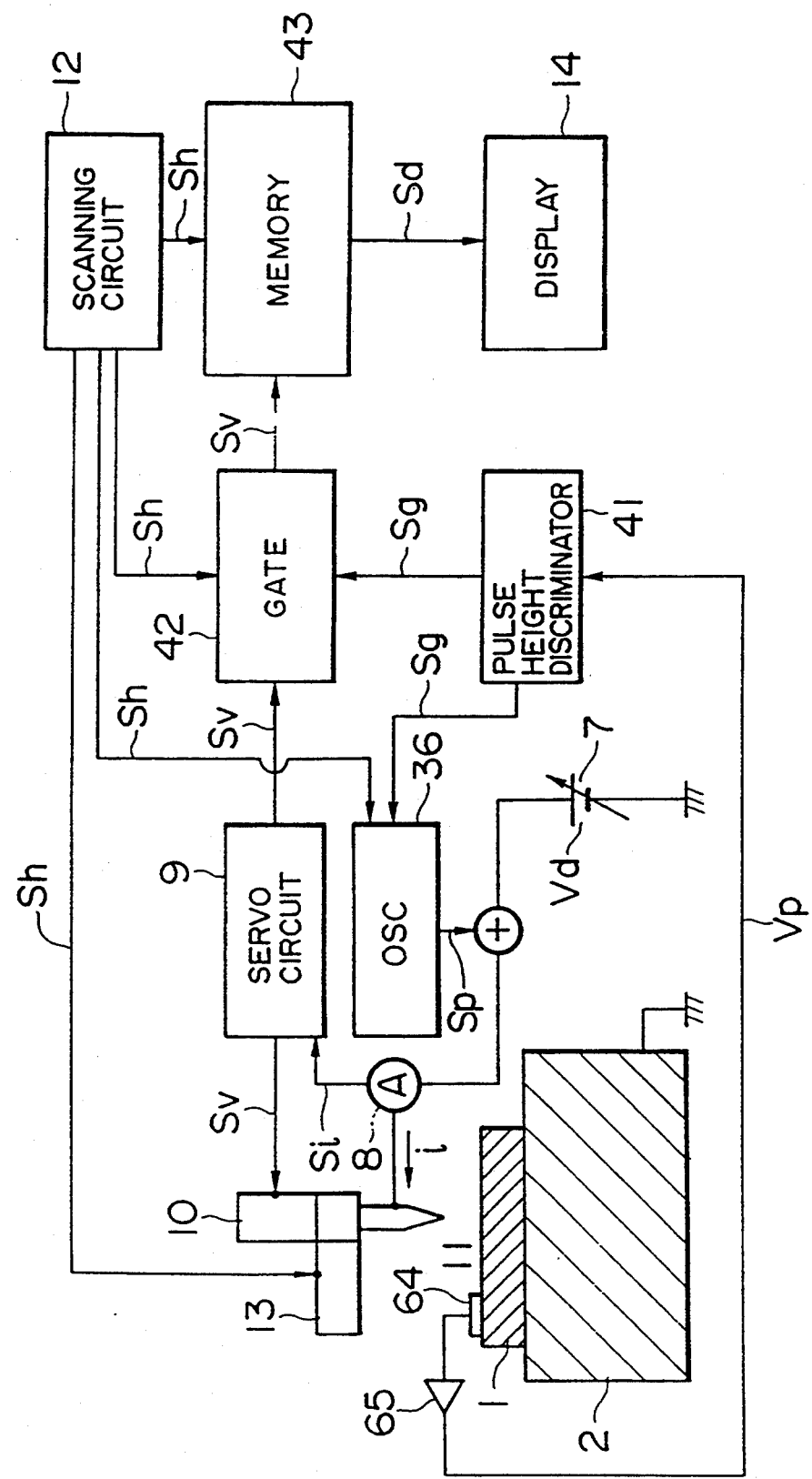

If the tunneling current is kept constant by modulating the gap voltage (i.e., voltage between the sample 1 and the tip 11) to displace the tip 11 for measuring the gap between the sample 1 and the tip 11 and always activating the servo circuit, the above described influence of strain is eliminated. This configuration is shown in FIG. 7. The strain detection system comprises a piezoelectric plate 64 attached to the surface of the sample 1 and an amplifier 65. By attaching the piezoelectric plate 64 to the surface of the sample 1 in this way, the detection efficiency of strain waves is improved in many cases. This is because a major portion of strain is transmitted along the surface.

A pulse $S_p$ similar to that of FIG. 5 is outputted from the oscillator 36 and added to the gap voltage $V_d$. This pulse $S_p$ is opposite in polarity to the gap voltage $V_d$. When the pulse $S_p$ is applied, the gap voltage decreases. In order to keep the tunneling current i constant at this time, the servo circuit 9 makes the tip 11 approach the sample 1. As the pulse becomes larger, the tip 11 further approaches the sample 1. When a certain pulse height is reached, the tip 11 comes into contact with the sample 1 and the oscillator 36 stops its output. A signal value $S_{vc}$ outputted from the servo circuit 9 at the time of contact is taken into the memory 43 because the gate 42 is opened by a gate signal $S_g$ supplied from the pulse height discriminator 41. On the other hand, a signal value $S_{vo}$ outputted from the servo circuit 9 when the pulse height is 0 immediately after the tip has been scanned by one pitch is similarly taken into the memory 43 because the gate 42 is opened by the scanning signl $S_n$ fed from the scanning circuit 12. The former signal $S_{vc}$ represents the real sample face, whereas the latter signal $S_{vo}$ represents the position of the tip 11 as the STM image signal. Difference $S_{vc}-S_{vo}$ between them corresponds to the vacuum gap value.

Figure 8:
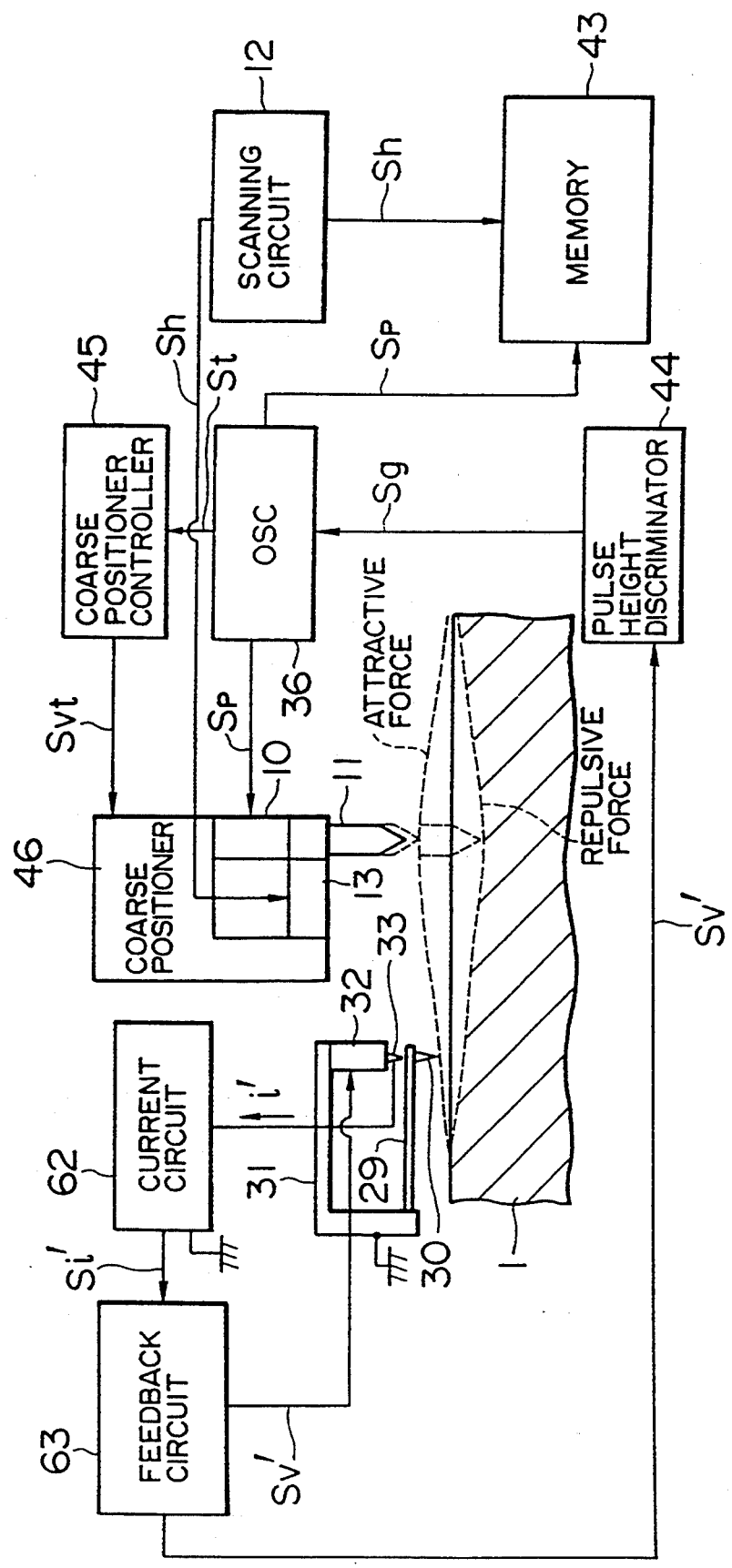
FIG. 8 is a block diagram showing a further embodiment of the present invention and a measurement state therein.

By using the above described gap measuring method, an insulator can be measured as shown in FIG. 8. In the apparatus configuration of that case, the power supply 7, the ammeter 8 and the servo circuit 9 shown in FIG. 6 become unnecessary, and the output pulse signal $S_p$ of the oscillator 36 is directly inputted to the Z-positioner 10. In the same way as FIG. 6, the STM scheme may be used as the strain detecting method. In that case, however, the sample surface near the tip 37 must be provided with conductivity by evaporating gold, for example. If the AFM scheme is used as shown in FIG. 8, processing for providing the sample face with conductivity is not necessary. Since the AFM scheme is similar to that of FIG. 3, its description will be omitted.

The operation will now be described by referring to FIGS. 8 and 9. The pulse $S_p$ shown in FIG. 5 is outputted from the oscillator 36 shown in FIG. 8 to the Z-positioner 10, and the tip 11 approaches the sample 1. In case strain is not detected even at the largest pulse height, a signal is outputted from the oscillator to a coarse positioner controller 45. Upon receiving a control signal $S_{vt}$ from the controller 45, a coarse positioner 46 makes the tip 11 approach the sample 1 by a distance not larger than the largest pulse height. From this state, the oscillator 36 outputs the pulse $S_p$ again. By this means, the tip 11 approaches the sample 1. If strain is detected at a certain pulse height, this number is stored into the memory 43. Immediately after that, the output pulse $S_p$ of the oscillator 36 becomes 0, and the tip 11 retracts. Succeedingly, the tip 11 is scanned by a distance corresponding to one pitch by the scanning circuit 12 and the scanner 13. At each pixel, the pulse number at the time when strain occurs is stored.

Figure 9:
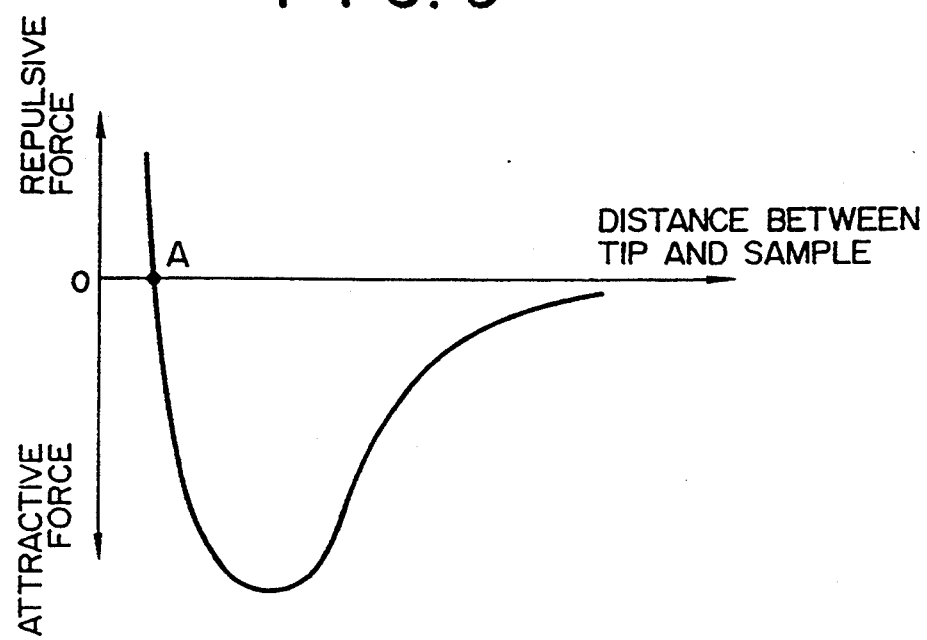
FIG. 9 is a curve diagram showing the atomic force.

FIG. 9 shows force exerted between atoms existing at the front end of the tip and atoms existing on the sample surface. While the tip 11 is approaching the sample 1, attractive force is exerted as far as a distance represented by A in FIG. 9. Further approach results in repulsive force. The strain observed first is attractive force, and the sample surface is raised. At a higher pulse, the surface is lowered by repulsive force. This situation is represented by broken lines in FIG. 8. Depending upon whether force is attractive or repulsive, the phase of the detected strain signal is inverted. By storing the number of the pulse $S_p$ in respective states pixel by pixel, it is possible to simultaneously obtain distribution of attractive force reflecting more intensely the influence of absorbed atoms and chemically active locations and distribution of repulsive force reflecting intensely atom positions of the sample itself. By level setting of a pulse height discriminator 44, magnitude of strain to be detected, i.e., strength of atomic force to be detected can be selected.

Figure 10:
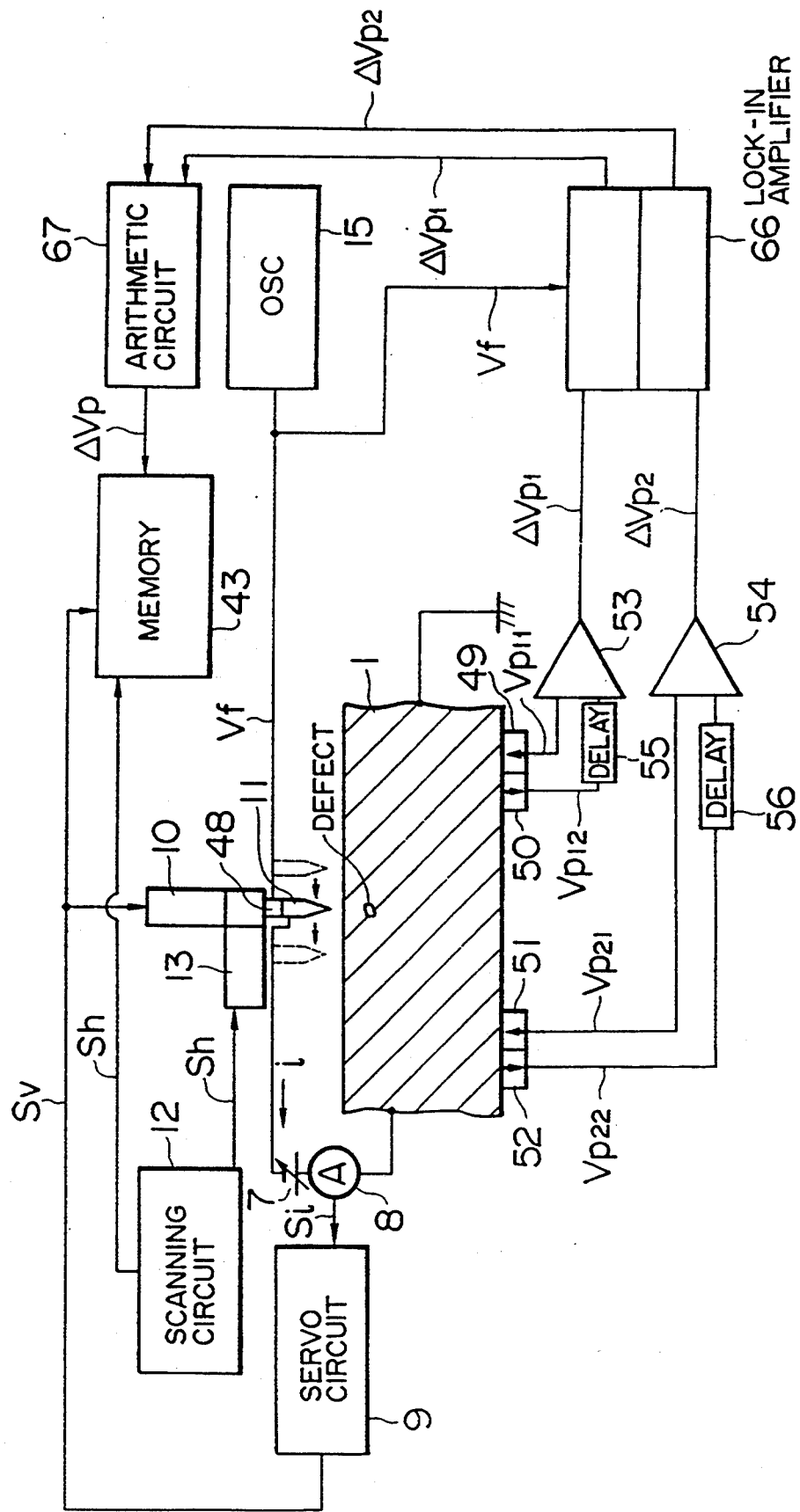

FIG. 10 shows an embodiment of observation of the inside of the sample using ultrasonic waves. Its basic configuration is the same as that of the STM. By the power supply 7, the ammeter 8, the servo circuit 9, the Z-positioner 10, the scanner 13 and the scanning circuit 12, the tip 11 is scanned while the tunneling current i is kept constant. A piezotransducer 48 is attached to the root of the tip 11. High frequency voltage $V_f$ having a frequency equivalent to the resonance frequency of the piezotransducer 48 is applied to the piezotransducer 48 by an oscillator 15. As a result, the tip 11 vibrates in a direction perpendicular to the sample face. From the contact point between the tip 11 and the sample 1, an ultrasonic wave is transmitted in the sample. This ultrasonic vibration is detected by piezoelectric plates 49, 50, 51 and 52 and differential amplifiers 53 and 54. Because of short wavelength, a slight phase difference is incurred between output signals $v_{p11}$ and $v_{p12}$ respectively of piezoelectric plates 49 and 50. A slight phase difference is also incurred between output signals $v_{p21}$ and $v_{p22}$ respectively of piezoelectric plates 51 and 52. These phase differences are compensated by delays 55 and 56. Output signals $\Delta v_{p1}$ and $\Delta v_{p2}$ respectively of the differential amplifiers 53 and 54 are inputted to a 2-channel lock-in amplifier 66. The output signal $v_f$ of the oscillator 15 is used as the reference signal of the lock-in amplifier 66. Output signals $\Delta V_{p1}$ and $\Delta V_{p2}$ of the lock-in amplifier 66 are inputted to an arithmetic circuit 67 to undergo subtraction, for example, therein. The result $\Delta V_p$ of subtraction is stored into the memory 43.

It is now assumed that the tip 11 is scanned from the right to the left of FIG. 10. In the sample 1, there is a defect (cavity) as illustrated, which reflects and scatters the ultrasonic wave. At a first broken line position, the output signal $\Delta V_{p1}$ of the differential amplifier 53 is larger than the output signal $\Delta V_{p2}$ of the differential amplifier 54. At the position of the tip represented by a solid line, $\Delta V_{p1}$ is equal to $\Delta V_{p2}$. At the last broken line position of the tip, the output signal $\Delta V_{p1}$ of the differential amplifier 53 becomes smaller than the output signal $\Delta V_{p2}$ of the differential amplifier 54. It is understood that the difference $\Delta v_p$ between signal intensities of the two differential amplifiers reflects the position of the defect (differential type).

Since the tip 11 is vibrated at a very high frequency in order to improve the resolution, the ammeter 8 is not able to measure the change of the tunneling current i caused by the vibration of the tip 11. Therefore, the STM feedback system is not affected at all.

In the present embodiment, two detection systems have been described. For obtaining a two-dimensional image, it is necessary to provide four detection systems and compare their signal intensities. Piezoelectric plates each having a small area as far as possible are used.

Figure 11:
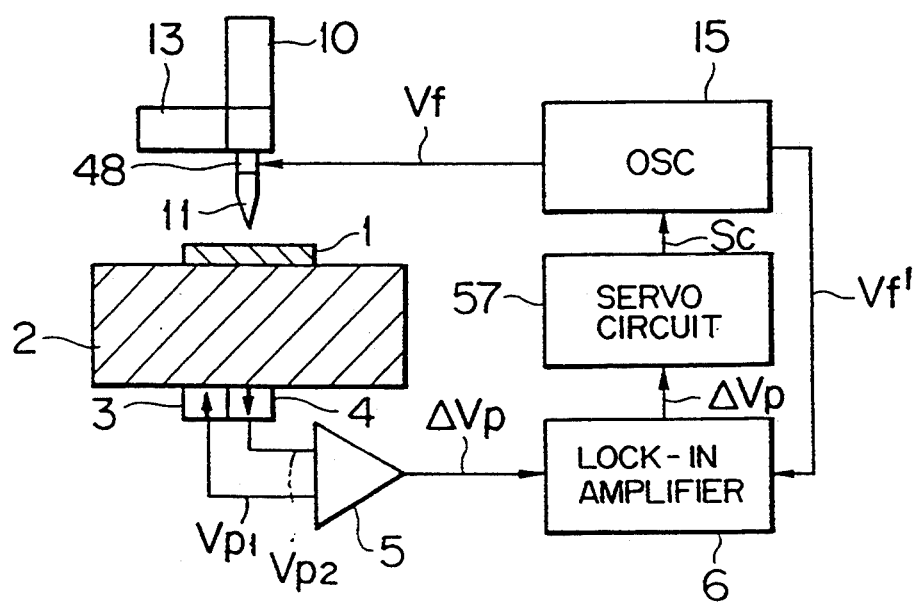
FIGS. 10, 11 and 12 are block diagrams respectively showing other embodiments of the present invention.

FIG. 11 shows configuration of an apparatus capable of continuously measuring the vacuum gap concurrently with STM imaging. Description of components relating to the STM will be omitted. In the state that the tunneling current is kept constant, the piezotransducer 48 is vibrated. The amplitude of strain waves caused by contact between the tip 11 and the sample 1 is detected as the output signal $\Delta v_p$ of the lock-in amplifier 6. A servo circuit 57 adjusts the amplitude of the output voltage $v_f$ of the oscillator 15 so that the signal $\Delta v_p$ may become constant. A reference signal $v_f'$ outputted from the oscillator 15 to the lock-in amplifier 6 always has a constant amplitude. The frequency of the piezotransducer 48 is higher than that of the feedback system of the STM. The STM is not affected in the same way as the above described embodiment.

Figure 12:
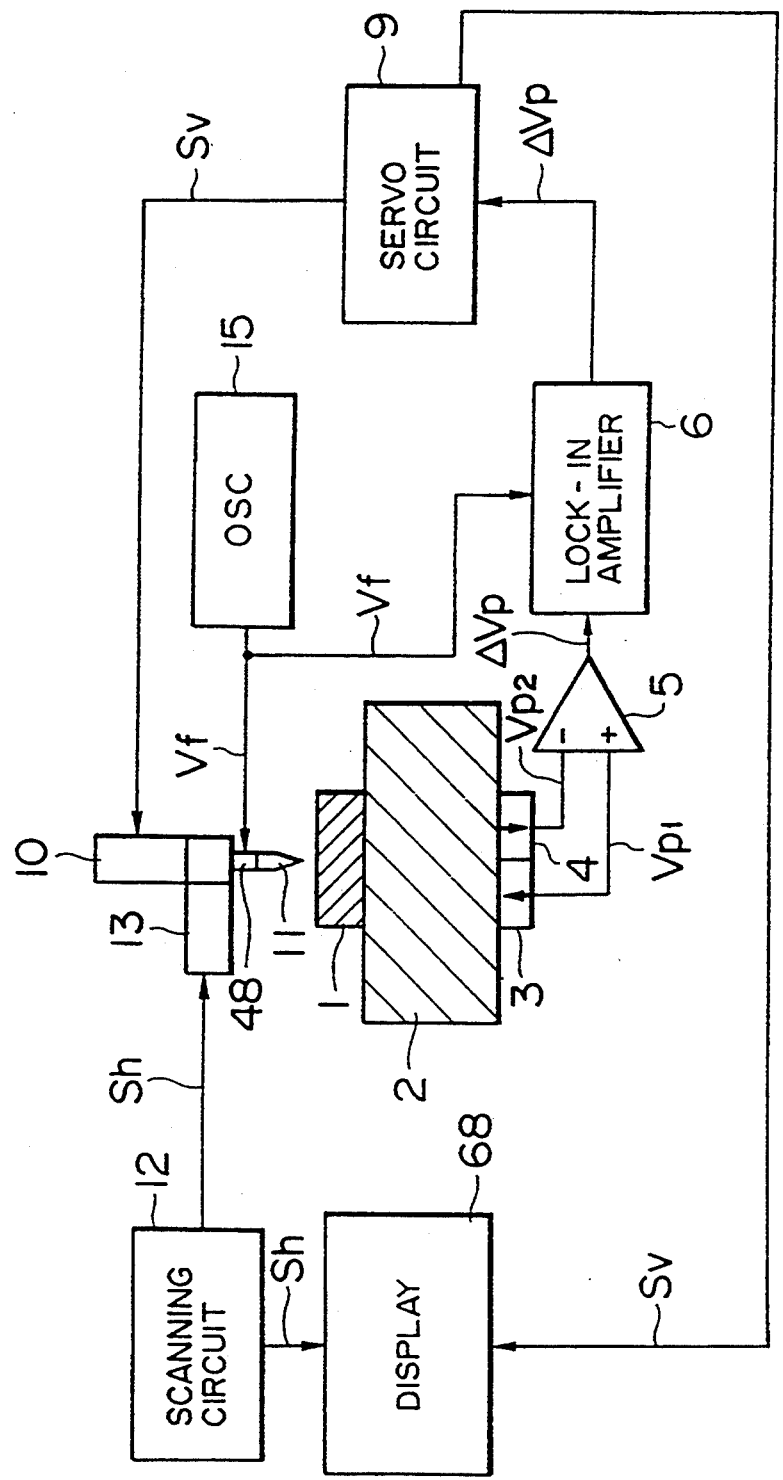

For observing an insulator sample, configuration of FIG. 12 is used. The output voltage $v_f$ of the oscillator 15 is constant. The servo circuit 9 controls the Z-positioner 10 to adjust the gap between the tip 11 and the sample 1 so that the output signal $\Delta v_p$ of the lock-in amplifier 6 may become constant. By displaying the displacement value $S_v$ of the Z-positioner 10 on a display 68 corresponding to the displacement value $S_h$ of the scanner 13, the surface shape of the insulator sample 1 is obtained.

In general, an image resulting from attractive force is obtained if the output signal $\Delta v_p$ of the lock-in amplifier 6 is kept at a small constant value. If a large value is set, an image resulting from repulsive force is obtained. Definite distinguishment between the attractive force and repulsive force is performed by the phase output of the lock-in amplifier 6. This is because the phase is inverted depending upon the force is attractive or repulsive.

Figure 13:
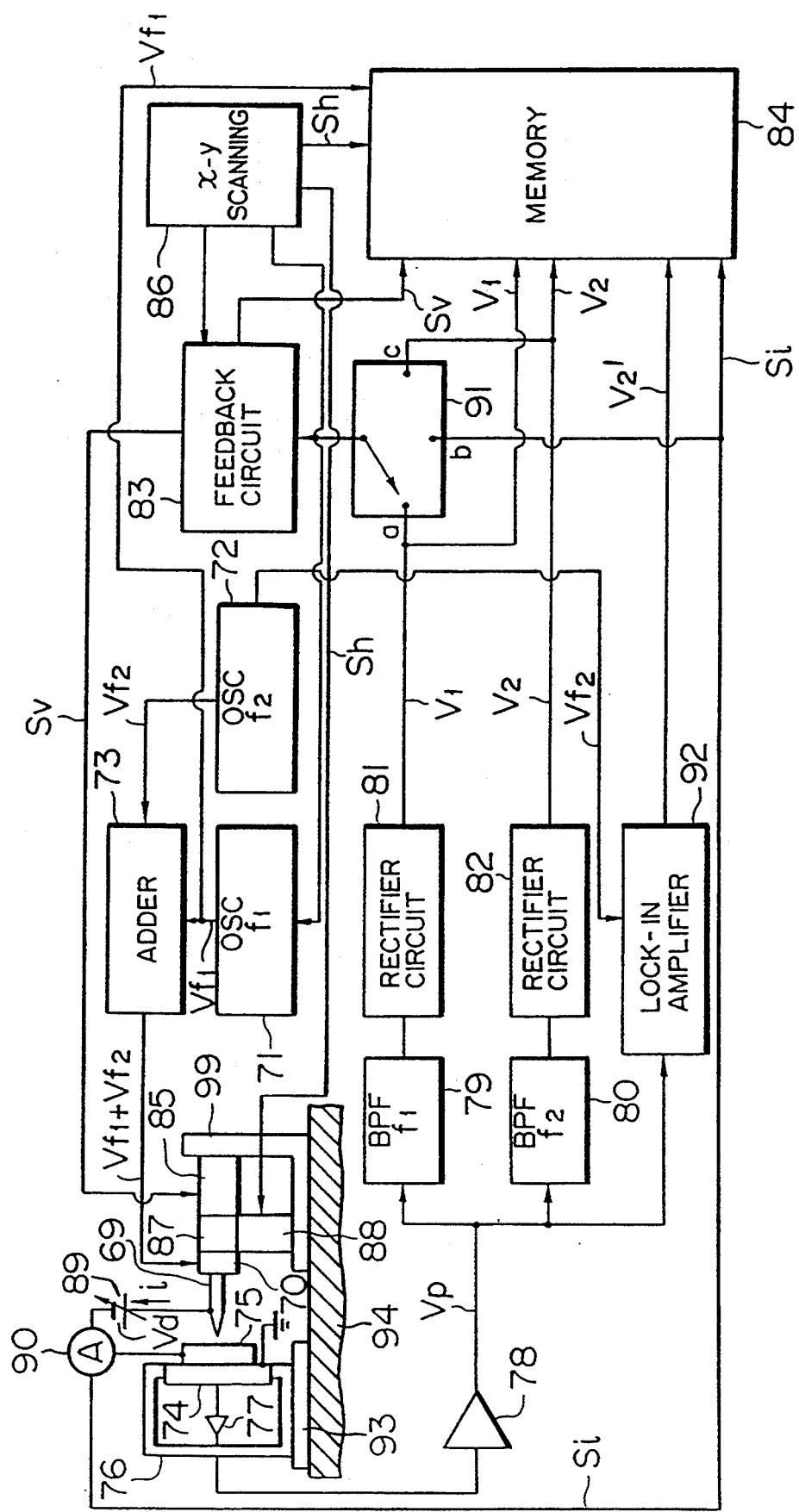
FIG. 13 is a block diagram showing another embodiment of the present invention.

In the above described two embodiments, the imaging time is short as compared with the methods shown in FIGS. 5, 6, 7 and 8. This is because the tip 11 is always vibrated and hence the servo circuit needs not be brought into the "hold" state. A more concrete embodiment of the present invention will now be described by referring to FIG. 13. A tip 69 having a keenly sharpened end is vibrated in the end direction by a piezotransducer 70. The vibration frequencies are so set by oscillators 71 and 72 as to be $f_1$ and $f_2$, respectively. Respective output voltages $v_{f1}$ and $v_{f2}$ are added by an adder 73 and the resultant sum signal is applied to a piezotransducer 70. Frequencies $f_1$ and $f_2$ are resonance frequencies of a piezoelectric plate 74. Because of difference in vibration mode, those frequencies are different each other by one digit or more (where $f_2 > f_1$). An elastic supporting plate 93 functions to prevent the vibration of the piezotransducer 70 from being transmitted through a stage 94 and arriving at the piezoelectric plate 74. A sample 75 is directly stuck on the piezoelectric plate 74. A shield box 76 functions to interrupt electrical noises. A preamplifier 77 is disposed within the shield box 76. Output signal $v_p$ of the piezoelectric plate 74 is amplified by an amplifier 78. Only frequency components of $f_1$ and $f_2$ are passed by two bandpass filters 79 and 80, respectively. These bandpass filters 79 and 80 are digital filters. Their passband width is very narrow, and their response speed is fast. Rectifier circuits 81 and 82 rectify AC voltages respectively passed through bandpass filters 79 and 80 and output the rectified voltages as DC voltages $v_1$ and $v_2$. The DC voltages $v_1$ and $v_2$ thus outputted are inputted to a feedback circuit 83 and a memory 84.

DC voltage $v_d$ is applied between the tip 69 and the sample 75 by power supply 89. The tunneling current i flowing between them is measured by an ammeter 90. The output signal $S_i$ of the ammeter 90 is inputted to the memory 84.

The feedback circuit 83 expands and contracts a Z-direction piezoelectric device 85 so that the input signal $v_1$, $v_2$ or $S_i$ may become a preset value. Switching of the input signal to the feedback circuit 83 is performed by a switch 91.

A scanning circuit 86 outputs the scanning signal $S_h$ to expand and contract an x-direction piezoelectric device 87 and a y-direction piezoelectric device 88. The scanning circuit 86 thus raster-scans the tip 69 along the sample 75 in a two-dimensional form. (In FIG. 13, however, scanning signals supplied to the x-direction piezoelectric device 87 and the y-direction piezoelectric device 88 are not illustrated separately.)

One end of each of the x, y and Z-direction piezoelectric devices 87, 88 and 85 is fixed to a frame 99. The other ends of those piezoelectric devices cross at one point, resulting in a tripod structure.

Into the memory 84 $v_1$, $v_2$, $S_i$ and the output signal $S_v$ of the feedback circuit 83 are so recorded as to correspond to the output signal $S_h$ of the scanning circuit 86, i.e., the position of the tip 69 on the sample 75 in the x-y plane. The $v_2$ and $S_i$ are so recorded as to correspond to the output voltage $v_{f1}$ of the oscillator 71 as well.

Figure 14:
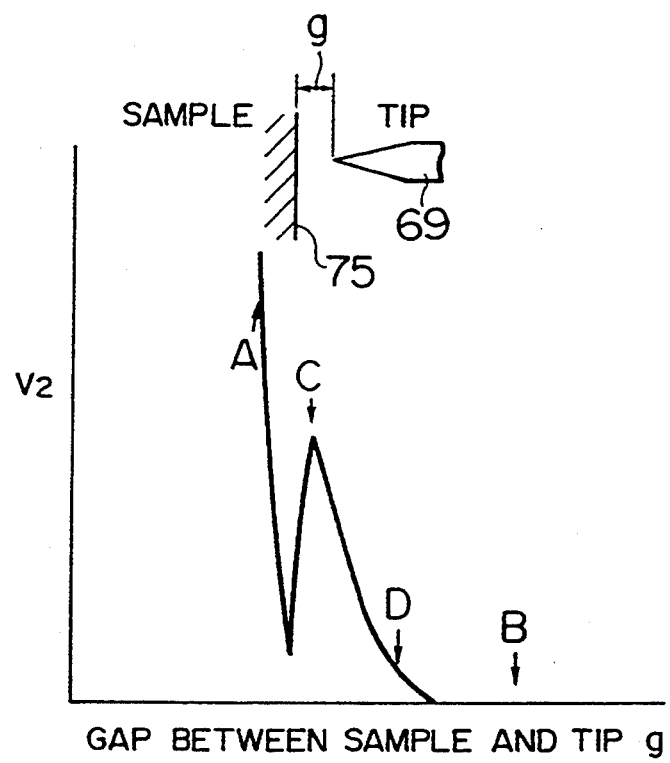
FIGS. 14 and 15 are curve diagrams showing measurement results obtained in the apparatus configuration of FIG. 13.

In the state that some force is exerted between the tip 69 and the sample 75, vibration of the tip 69 is transmitted to the sample 75 and detected as the output signal $v_p$ of the piezoelectric plate 74 (and hence its frequency components $v_1$ and $v_2$). First of all, the atomic force will now be described. In this case, $v_d$ is set at 0 volt. FIG. 14 shows a typical example of measurement of the output signal $v_2$ of the rectifier circuit 82. The amplitude of vibration of the tip 69 caused by the output signal $v_{f2}$ of the oscillator 72 is as small as 0.1 nm to several nm at the maximum. On the other hand, the amplitude of vibration of the tip 69 caused by the output signal $v_{f1}$ of the oscillator 71 is equivalent to the distance from A to B shown in FIG. 14. Since the output signal $v_1$ of the rectifier circuit 81 is kept constant by expansion and contraction of the Z-piezoelectric device 85 caused by the feedback circuit 83, the points A and B are kept at illustrated positons.

In FIG. 14, magnitude of attractive force is indicated in the range B to C. If the tip 69 approaches the sample 75 beyond the point C, repulsive force is suddenly exerted. The $v_2$ temporarily decreases from the point C because the phase difference of electromotive force caused by attractive force is opposite to that caused by repulsive force.

Figure 15:
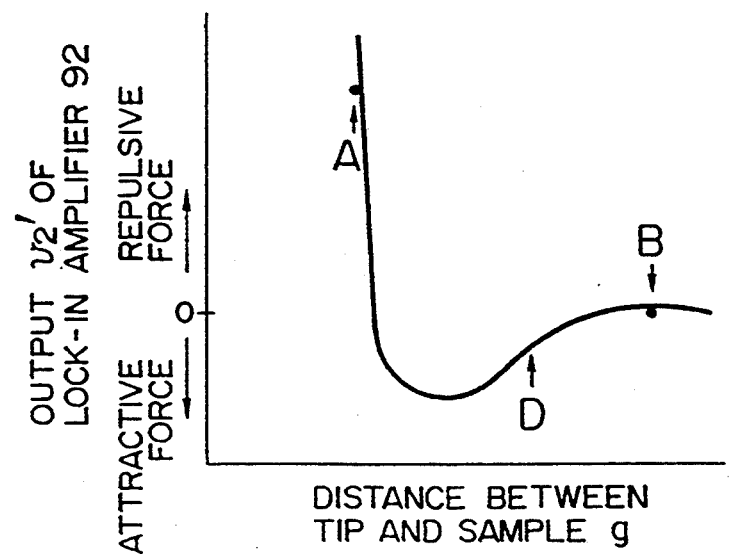

If a lock-in amplifier 92 is used instead of the bandpass filter 80 and the rectifier circuit 82, not only amplitude but also phase information is simultaneously obtained. Therefore, atomic force distribution as shown in FIG. 15 is obtained.

Atomic force distribution for respective points on the sample 75 (i.e., the value of $v_2$ corresponding to the gap between the sample 75 and the tip 69, or the value of output signal $v_2'$ of the lock-in amplifier 92) is stored into the memory 84. At the same time, the signal $S_v$ depending upon the displacement value of the Z-direction piezoelectric device 85 is inputted from the feedback circuit 83 to the memory 84 and is stored therein. These two kinds of information is so stored as to correspond to the scanning signal $S_h$ fed from the x-y scanning circuit 86. As a result, two dimensional distribution on the sample face is obtained. Three dimensional distribution of atomic force is thus obtained. The signal $S_v$ fed from the feedback circuit 83 represents the surface shape of the sample 75. Resolution of atom order is obtained.

By setting the voltage $v_d$ of the power supply 89 at a suitable value and recording the measurement signal $S_i$ of the tunneling current i concurrently with the output signal $v_2$, the electric characteristic can be known. If $v_d$ is set at several volts, for example, field emission resonance is observed. This is a phenomenon that the tunneling current i vibrates with respect to $v_{f1}$ (gap between the tip 69 and the sample 75) and reflects the wavelength and phase of the current. This is described in Physical Review letters, Vol. 55, No. 9, 1985, pp. 987 to 990.

When field emission resonance is measured, it is desirable to set the output $v_{f2}$ of the oscillator 72 at 0.

By obtaining three dimensional distribution of atomic force, it is possible to know the bonding state of atoms near the surface irrespective of conductivity of the sample. Further, it is also possible to know the bonding state of absorbed molecules on the sample surface, kind of absorbed molecules and change of sample surface state caused by absorption.

The present embodiment is a very important means in studying chemical reaction. For example, an arbitrary material is applied onto the sample 75, and another material bonded to a particular part of the material applied onto the sample 75 is applied to the tip 69. Three dimensional distribution of atomic force is then measured. Since the extent of atomic force (attractive force) is large and the force is strong at the bonding part, the position of the bonding part can be known. Further, if platinum or the like is used for the tip 69, its catalytic effect is made clear.

If the switch 91 is set at position c and the Z-direction piezoelectric device 85 is expanded and contracted so that the signal $v_2$ fed from the rectifier circuit 82 may become constant, scanning once yields only a curved surface formed by atomic force having a specific magnitude, which is set in the feedback circuit 83. If the position of the tip 69 in the Z direction is so controlled that the value of $v_2$ at a point D shown in FIG. 14 may be maintained, for example, distribution of attractive force is obtained. If $v_2$ is set at the point A, distribution of repulsive force is obtained. The distribution of repulsive force nearly corresponds to lattice points (atom positions). At locations where the extent of attractive force is wide, chemical activities or absorbed molecules exist. By making those locations correspond to the distribution of repulsive force, the extent of attractive force of each atom can be easily judged. By setting $v_d$ suitably and simultaneously recording i, the electric characteristic of the sample 75 can be obtained.

The case where magnetic force is exerted between the tip 69 and the sample 75 will now be described. The tip 69 comprises a ferromagnetic material and has an end so sharpened by electrolytic polishing as to have a diameter nearly equivalent to 0.1 μm. Information of the sample 75 to be observed comprises the magnetic domain structure of the magnetic material and its surface shape. The switch 91 is set at position a. Since $v_1$ is kept constant, the signal $S_v$ outputted from the feedback circuit 83 to the memory 84 represents the shape of sample surface.

Whereas the arrival distance of atomic force is 1 nm to approximately 10 nm at its maximum, the leakage magnetic field typically exists at a far greater distance than this. As a result, vibration of the tip 69 caused by $v_{f1}$ induces the component $v_1$ of electromotive force of the piezoelectric plate 74 via only magnetic force. In this state, however, the surface shape of the sample 75 cannot be obtained. Therefore, $v_1$ such as $v_{1c}$ to be kept constant by the feedback circuit 83 is set at a sufficiently large value so that it may not be generated unless atomic force (repulsive force) is sensed. As a result, the signal $S_v$ supplied from the feedback circuit 83 to be so recorded as to correspond to the scanning signal $S_h$ supplied from the x-y scanning circuit 86 represents the surface shape.

The output signal $v_2$ supplied from the rectifier circuit 82 with respect to the gap between the tip 69 and the sample 75, which changes depending upon the AC output voltage $V_{f1}$ fed from the oscillator 71, represents the differential magnetic force distribution perpendicular to the surface of the sample 75. By recording this differential magnetic force distribution so as to correspond to the scanning signal $S_h$ of the x-y scanning circuit 86, three dimensional magnetic force distribution is obtained.

By lowering the response speed of the rectifier circuit 82 as low as the frequency of approximately $f_1$, $v_2$ becomes an averaged value of the differential magnetic force distribution perpendicular to the surface of the sample 75. Although the resolution in the perpendicular direction is thus lost, the magnetic domain structure can be specified.

Further, with respect to the scanning signal of each pixel of the x-y scanning circuit 86, the output signal $S_v$ from the feedback circuit 83 to the Z-direction piezoelectric device 85 undergoes holding (i.e., the value at that instant is held). Further, the value of $v_{f1}$ is held at constant voltage $V_{f1c}$. The method of recording the value of $v_2$ at the position of the tip 69 at that time is also adopted. In this case, the gap between the tip 69 and the sample 75 is defined by the voltage $V_{f1c}$ which should be set, and the differential magnetic force at this position is obtained as $v_2$. For that purpose, it is necessary to hold the tip 69 at such a position that atomic force is not exerted between the tip 69 and the sample 75. If $v_{f1c}$ is changed during holding and $v_2$ is recorded for respective values of $v_{f1c}$, differential magnetic force distribution perpendicular to the surface of the sample 75 is obtained. This technique can also be widely used for applications other than magnetic force measurement, and this technique is convenient in case the response speed of the electric circuit system including the bandpass filter 80, the rectifier circuit 82 and the memory 84 is slow.

As shown in FIG. 15, phase information of the output signal force $v_2$ (component of frequency $f_2$) of the piezoelectric plate 74 with respect to the output signal $v_{f2}$ of the oscillator 72 is also obtained from the information $v_2'$ supplied from the lock-in amplifier 92. From this phase information, the direction of the magnetic line of force can also be specified. In this case, however, the tip 69 must be formed by using such a magnetic material that the magnetic domain is not changed by the leakage magnetic field coming from the sample 75. Before this tip 69 is mounted on the apparatus, the tip 69 is so heated in the external magnetic field in the front end direction to the Curie temperature or higher and then returned to the room temperature. As a result, the magnetic domain at the end of the tip 69 is aligned in the direction of the external magnetic field (i.e., direction of front end). It is understood that the leakage magnetic field of the sample 75 has a magnetic field component in the front end direction of the tip 69 in case attractive force is exerted between the tip 69 and the sample 75 whereas the leakage magnetic field has a magnetic field component of opposite direction in case of repulsive force.

In case of a conductive sample, the tip 69 may be vibrated with only a single frequency $f_2$ by setting the switch 91 at position b and implementing the function of tracing the surface of the sample 75 by means of the conventional STM scheme. The voltage $v_d$ is applied between the tip 69 and the sample 75 by the power supply 89, and the tunneling current i flowing between them is measured by the ammeter 90. The feedback circuit 83 applies the voltage $S_v$ to the Z-direction piezoelectric device 85 so that the tunneling current i becomes constant, whereby the gap between the tip 69 and the sample 75 is controlled. By the function of the x-y scanning circuit 86, the x-direction piezoelectric device 87 and the y-direction piezoelectric device 88, the tip 69 is scanned to trace the face of the sample 75. The surface shape of the sample 75 is recorded into the memory 84.

It is said that the gap between the tip 69 and the sample 75 is kept at approximately 1 nm in an STM. AC voltage $v_{f2}$ fed from the oscillator 72 is applied to the piezotransducer 70. As a result, the tip 69 vibrates. However, the amplitude of vibration is limited to 1 nm or less, and strong atomic force (repulsive force) is not exerted between the tip 69 and the sample 75. Force transmitting the vibration of the tip 69 to the sample 75 is mainly magnetic force. The electromotive force $v_2$ of the piezoelectric plate 74 corresponding to the scanning signal $S_h$ supplied from the x-y scanning circuit 86 indicates the magnetic force distribution on the surface of the sample 75.

In the present embodiment, magnetic force distribution in the state that the tip 69 is extremely close to the sample 75 is obtained, resulting in high resolution.

Figure 16:
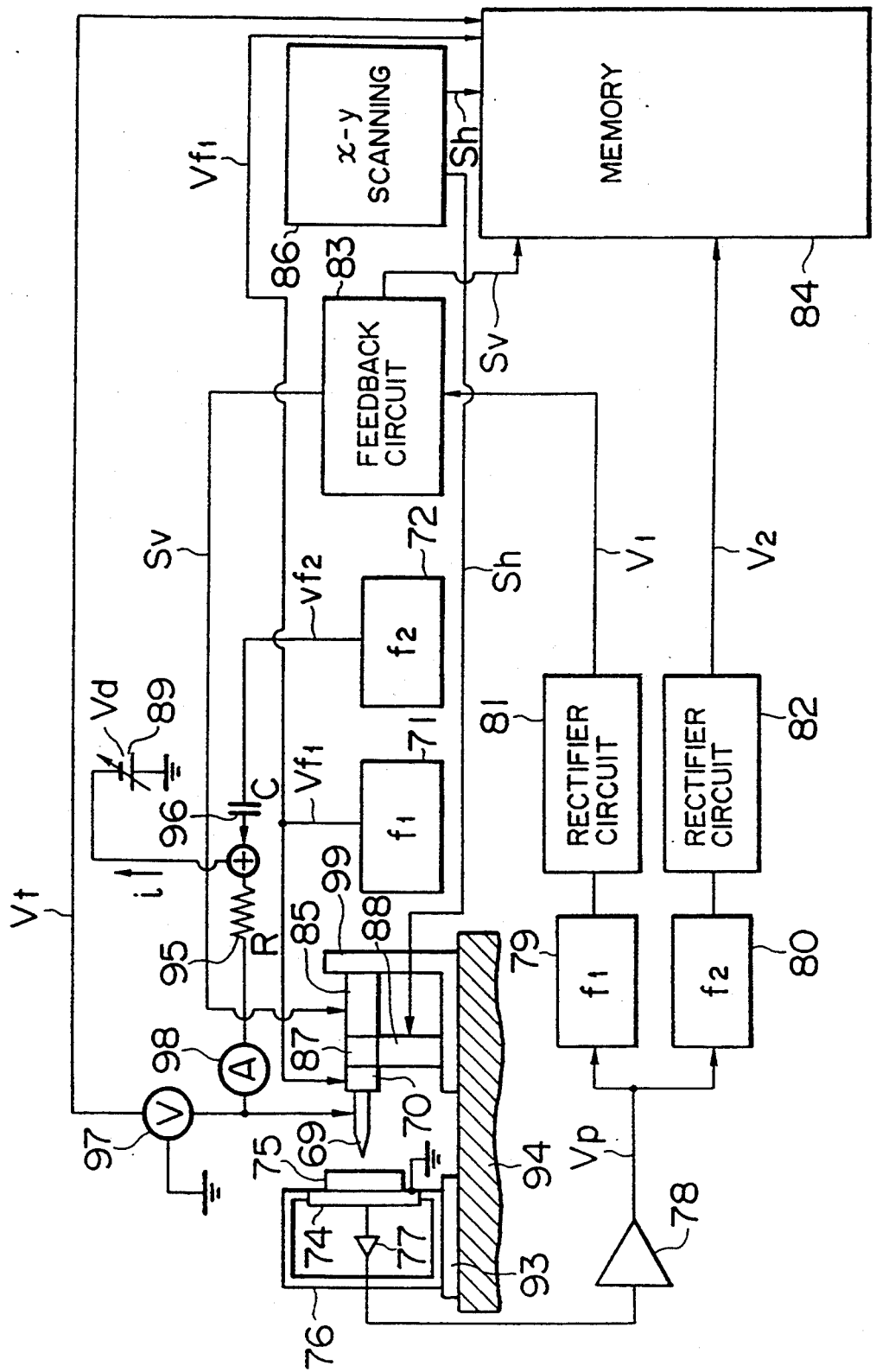
FIGS. 16 and 17 are block diagrams respectively showing other embodiments of the present invention.

FIG. 16 shows apparatus configuration for measuring electric force. AC voltage $v_{f1}$ fed from the oscillator 71 is applied to the piezoelectric transducer 70 to vibrate the tip 69. The Z-direction piezoelectric device 85 is expanded and contracted by the feedback circuit 83 so that the electromotive force $v_1$ of the piezoelectric plate 74 may be kept constant. The feedback system for this purpose is the same as that of FIG. 13. In the present embodiment, the AC voltage $v_{f2}$ supplied from the oscillator 72 is applied to the tip 69 in addition to the DC voltage $V_d$. As a result, an electric field changing with the frequency $f_2$ is formed between the tip 69 and the sample 75. So long as charges are not trapped in the sample 75, attractive force depending upon the electric field strength is exerted between the tip 69 and the sample 75. Arbitrary DC voltage $v_d$ supplied from the power supply 89 is added to $v_{f2}$ and then applied to the tip 69. Voltage $v_t$ of the tip 69 is measured by a voltmeter 97. If a current does not flow between the tip 69 and the sample 75, $v_t$ becomes nearly equivalent to $v_d + v_{f2}$. An ammeter 98 measures the current between the tip 69 and the sample 75.

If the sample 75 is metal, an electric field exists only between the tip 69 and the sample 75. A resistor R95 and a capacitor C96 function to prevent a large current from flowing between the sample 75 and the tip 69 when the sample 75 strongly comes in contact with the tip 69. Electrical attractive force causing strain depends upon the electrostatic capacity and voltage of the tip 69 and the sample 75. Therefore, distribution of $v_2$ with respect to the scanning signal $S_h$ reflects the thickness or the like of an oxide layer (insulation layer) formed on the surface of the sample (metal) 75.

If the sample 75 is a semiconductor sample, an electric field exists within the sample 75 as well. The electrostatic capacity between the tip 69 and the sample 75 changes with the voltage value $v_d$ of the power supply 89 or the voltage $v_{f2}$ fed from the oscillator 72. Further, charges are trapped near the surface oxide layer. Therefore, $v_2$ provides information such as the kind of major carriers of the semiconductor (i.e., whether the major carriers are electrons or holes, for example), their density distribution and carriers trapped near the surface oxide layer. For this purpose, it is necessary to record values of $v_2$ corresponding to the scanning signal $S_h$ from the x-y scanning circuit 86, $v_{f1}$ and $v_{t1}$ respectively, into the memory 84.

In case of an insulator sample, it is desirable to make the thickness of the sample 75 very thin. This is because electric force becomes weak and at the same time the spatial distribution of $v_2$ is hard to obtain because the electric field formed by $v_{f2}$ and $v_t$ exists in a wide region ranging from the end of the tip 69 to the reference potential (ground potential) of the rear face of the sample 75 (i.e., the surface of the piezoelectric plate 74). The voltage $v_2$ reflects the dielectric constant of the sample 75 or trapped charges.

In the present embodiment, force exerted between the tip 69 and the sample 75 is detected. As compared with the technique of detecting electrostatic capacity, therefore, the resolution is higher. This is because force is more sensitive to the gap between the tip 69 and the sample 75 as compared with electrostatic capacity.

When the piezoelectric plate 74 is attached to the front face of the sample 75 (i.e., the face wherewith the tip 69 is in contact), the sensitivity becomes higher. However, it is effective in knowing the elastic characteristic to attach the piezoelectric plate 74 to the rear face of the sample 75 because the strength of the strain signal (such as $v_1$ or $v_2$) largely differs depending upon the elastic characteristic of the sample 75. For example, it is convenient for identifying a region on a silicon wafer whereto chemical processing has already been applied.

Measurement of domain of a piezoelectric thin film will now be described. A piezoelectric thin film is mounted as the sample 75 of FIG. 16. As a result of applying an AC electric field having a frequency $f_2$, the piezoelectric thin film expands and contracts, and the resultant vibration is detected as $v_2$. The $v_2$ in this case represents the piezoelectric constant of a minute region of the sample 75. If $f_2$ is set as the resonance frequency in the thickness direction of the piezoelectric thin film, $v_2$ changes as the thickness of the thin film changes extremely slightly. the thickness distribution can thus be known. If the phase difference of electromotive force (component of the frequency $f_2$) of the piezoelectric plate 74 with respect to $vf_2$ is detected by using a lock-in amplifier (phase detection), the direction of domain can be distinguished. This is because the phase difference also differs by 180° if the direction of domain differs by 180°.

Figure 17:
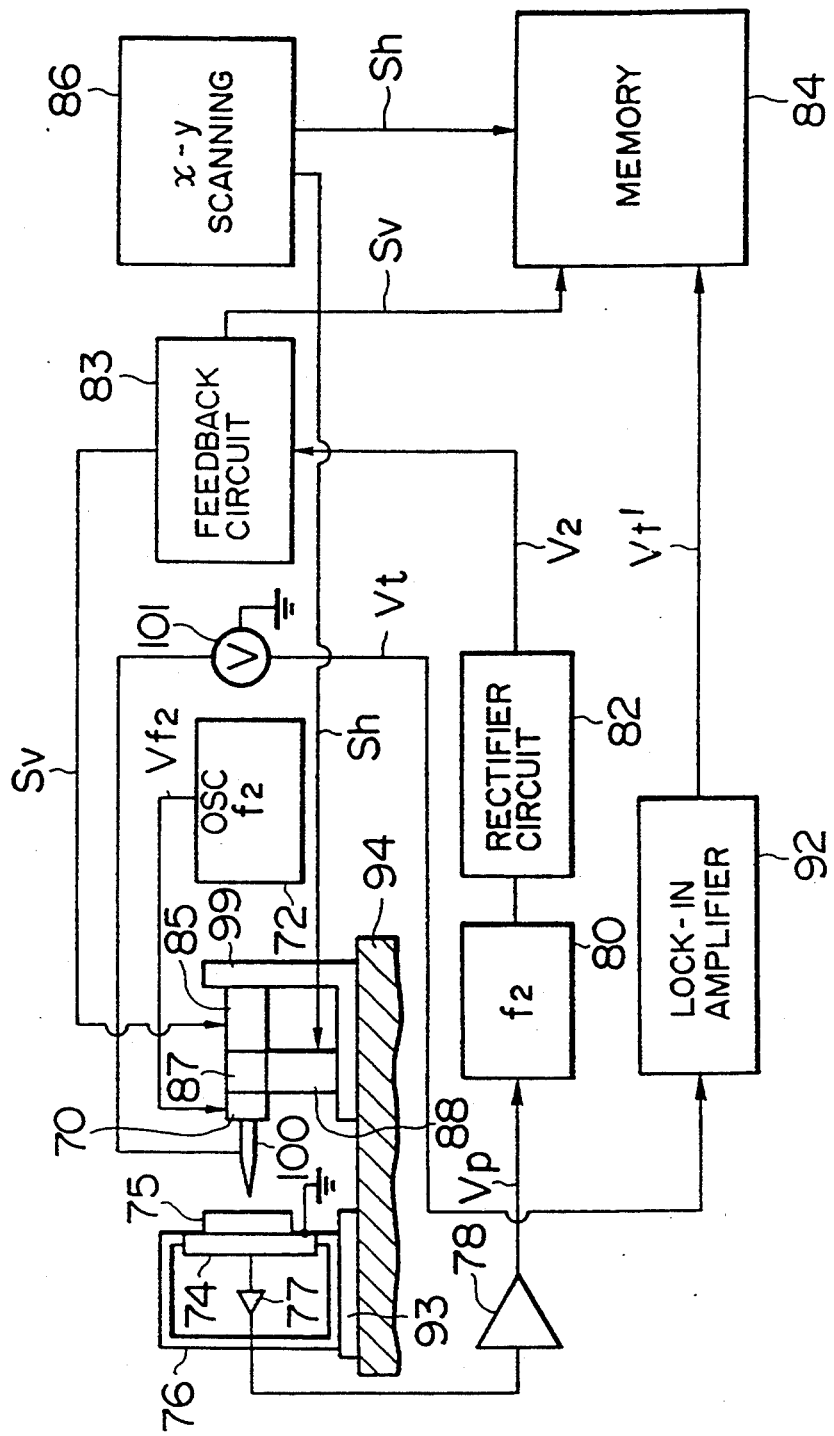

FIG. 17 shows an example in which a tip (probe tip) 100 is used as the electrode for measuring the potential on the surface of the sample 75. The output voltage $v_{f2}$ (frequency $f_2$) of the oscillator 72 is applied to the piezoelectric transducer 70 to vibrate the metal probe tip 100 having a keenly sharpened front end in the front end direction. Strain caused in the sample by the interaction between the probe tip 100 and the sample 75 is detected as electromotive force of the piezoelectric plate 74, amplified by the preamplifier 77 and the amplifier 78, and then inputted to the bandpass filter 80. The bandpass filter 80 outputs only the component of the frequency $f_2$ to the rectifier circuit 82. Its amplitude $v_2$ is outputted from the rectifier circuit 82 to the feedback circuit 83. The feedback circuit 83 keeps $v_2$ at a preset fixed value by expanding and contracting the Z-direction piezoelectric device 85. The potential $V_t$ of the probe tip 100 is measured by a voltmeter 101 and inputted to a lock-in amplifier 92. The reference frequency of the lock-in amplifier 92 is $f_2$, and the amplitude of the potential $V_t$ of the probe tip 100 and the phase difference of $v_t$ with respect to the output signal $v_{f2}$ are outputted. The x-y scanning circuit 86 raster-scans the probe tip 100 along the face of the sample 75 in a two-dimensional form by expanding and contracting the x-direction piezoelectric device 87 and the y-direction piezoelectric device 88. The output signal $S_v$ of the feedback circuit 83 and the output signal $v_t'$ of the lock-in amplifier 92 are so recorded into the memory 84 as to correspond to the scanning signal $S_h$.

Distribution of the output signal $S_v$ of the feedback circuit 83 represents the surface shape of the sample 75. Distribution of the output signal $v_t'$ of the lock-in amplifier 92 indicates the potential distribution on the surface of the sample 75. In a sample of a piezoelectric thin film, for example, amplitude information of the output signal $v_t'$ of the lock-in amplifier 92 represents the piezoelectric constant, whereas phase information represents the direction of polarization. Therefore, this example is effective in measuring potential distribution under the operation state of a minute electronic device.

As evident from the foregoing detailed description, the present invention provides information regarding inside of crystals such as internal stress.

Further, since the vacuum gap can be measured concurrently with the STM measurement, the surface state and the electron state of the sample can be known.

In observation of an insulator surface, images formed by attractive force, which cannot be obtained by a conventional AFM, are obtained.

What is claimed is:

1. A surface measuring apparatus comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
a holding mechanism for temporarily putting the operation of said feedback mechanism in a holding state;
second detecting means for detecting second physical information acting between said sample and said probe in a second state of said probe during said holding state;
means for separately displaying (a) at least one of an output signal of said feedback mechanism and an output of said first detecting means in said first state of said probe and (b) an output of said second detecting means in said second state of said probe in association with a signal from said scanning mechanism.

2. A surface measuring apparatus according to claims 1, wherein said first and second states of said probe are different from each other in a vibration amplitude of said probe.

3. A surface measuring apparatus according to claim 1, wherein said probe in said second state of said probe is at a more remote position from the sample surface than said probe in said first state in a direction perpendicular to the sample surface.

4. A surface measuring apparatus according to claim 1, wherein an AC voltage is applied to said probe in said second state of said probe.

5. A surface measuring apparatus according to claim 1, wherein the first and second physical information detected in said first and second states of said probe includes a physical quantity of a phenomenon occurring by vibrating said probe.

6. A surface measuring apparatus according to claim 3, wherein the second physical information detected in said second state of said probe includes magnetic information between said probe and said sample.

7. A surface measuring apparatus according to claim 1, wherein the first physical information detected in said first state of said probe includes a force acting substantially between said probe and said sample.

8. A surface measuring apparatus according to claim 1, wherein the first physical information detected in said first state of said probe includes a tunneling current between said probe and said sample.

9. A surface measuring apparatus according to claim 2, wherein said probe is at a more remote position from the sample surface in said second state than said probe is from the sample surface in said first state of the probe in a direction perpendicular to the sample surface.

10. A surface measuring apparatus according to claim 2, wherein the first and second physical information detected in said first and second states of said probe includes a physical quantity of a phenomenon occurring by vibrating said probe.

11. A surface measuring apparatus according to claim 9, wherein the second physical information detected in said second state of said probe includes magnetic information between said probe and said sample.

12. A surface measuring apparatus according to claim 2, wherein the first physical information detected in said first state of said probe includes a force acting substantially between said probe and said sample.

13. A surface measuring apparatus comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
a holding mechanism for temporarily placing the operation of the feedback mechanism in a holding state;
second detecting means for detecting second physical information acting between said sample and said probe in a second state of said probe during said holding state;
means for separately displaying (a) at least one of an output signal of said feedback mechanism and an output of said first detecting means in said first state of said probe and (b) an output of said second detecting means in said second state of said probe during said holding state in association with an output of said scanning mechanism.

14. A surface measuring apparatus according to claim 13, wherein the first physical information detected in said first state of said probe includes a tunneling current between said probe and said sample.

15. A surface measuring apparatus, comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
second detecting means for detecting second physical information acting between said sample and said probe in a second state of said probe; and
means for separately displaying (a) at least one of an output signal of said feedback mechanism and an output of said first detecting means in said first state of said probe and (b) an output of said second detecting means in said second state of said probe in association with an output of said scanning mechanism;
wherein said first and second states of said probe are different from each other in vibration amplitude of said probe.

16. A surface measuring apparatus, comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
second detecting means for detecting second physical information acting between said sample and said probe in a second state of said probe; and
means for separately displaying (a) at least one of an output signal of said feedback mechanism and an output of said first detecting means in said first state of said probe and (b) an output of said second detecting means in said second state of said probe in association with an output of said scanning mechanism;
wherein said probe is at a more remote position from the sample surface in said second state of said probe is from the sample surface is said first state of said probe, in a direction perpendicular to said sample surface.

17. A surface measuring apparatus according to claim 16, wherein the second physical information detected in said second state of said probe includes magnetic information between said probe and said sample.

18. A surface measuring apparatus comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
second detecting means for detecting second physical information acting between said sample and said probe in a second state of said probe; and
means for separately displaying (a) at least one of an output signal of said feedback mechanism and an output of said first detecting means in said first state of said probe and (b) an output of said second detecting means in said second state of said probe during said holding state in association with an output of said scanning mechanism;
wherein an AC voltage is applied to said probe in said second state of a said probe.

19. A surface measuring apparatus comprising:
a sample;
a probe having a keenly sharpened tip disposed in an opposing relation to said sample;
a scanning mechanism to scan said probe or said sample relatively and two-dimensionally;
first detecting means for detecting first physical information acting between said sample and said probe in a first state of said probe;
a feedback mechanism for controlling a distance between said sample and said probe in accordance with said detected first physical information;
second detecting means for detecting second physical information acting between said sample and said probe in a second state of said probe; and
means for separately displaying (a) at least one of an output signal of said feedback mechanism and an output of said first detecting means in said first state of said probe and (b) an output of said second detecting means in said second state of said probe in association with an output of said scanning mechanism;

wherein the first and second physical information detected in said first and second states of said probe includes a physical quantity of phenomenon occurring by vibrating said probe.

20. A surface measuring apparatus comprising:

a sample;

a probe having a keenly sharpened tip disposed in an opposing relation to said sample;

a scanning mechanism to scan said probe or said sample relatively and two-dimensionally;

first detecting means for detecting first physical information acting between said sample and said probe in a first state of said probe;

a feedback mechanism for controlling a distance between said sample and said probe in accordance with said detected first physical information;

second detecting means for detecting second physical information acting between said sample and said probe in a second state of said probe; and means for separately displaying (a) at least one of an output signal of said feedback mechanism and an output of said first detecting means in said first state of said probe and (b) an output of said second detecting means in said second state of said probe in association with an output of said scanning mechanism;

wherein the first physical information detected in said first state of said probe includes a force acting substantially between said probe and said sample.

* * * * *